United States Patent
Becher et al.

(10) Patent No.: US 6,280,766 B1
(45) Date of Patent: *Aug. 28, 2001

(54) METHOD FOR TRANSDERMAL APPLICATION OF ACTIVE SUBSTANCES AT HIGH CONSTANT DOSAGE

(75) Inventors: Frank Becher, Koblenz; Werner Wessling, Rengsdorf, both of (DE)

(73) Assignee: LTS Lehman Therapie-Systeme GmbH, Neuwied (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/549,887

(22) Filed: Apr. 17, 2000

Related U.S. Application Data

(63) Continuation-in-part of application No. 09/173,804, filed as application No. PCT/EP98/06607 on Oct. 19, 1998, now Pat. No. 6,143,320.

(30) Foreign Application Priority Data

Oct. 18, 1997 (DE) .............................................. 197 46 191

(51) Int. Cl.⁷ ............................ A61F 13/00; A61L 15/16; A01N 43/42

(52) U.S. Cl. ............................ 424/449; 424/447; 514/282

(58) Field of Search ..................................... 424/449, 456, 424/484; 514/847, 969, 881

(56) References Cited

U.S. PATENT DOCUMENTS

| | | | |
|---|---|---|---|
| 5,026,556 | 6/1991 | Drust et al. | 424/449 |
| 5,362,496 | 11/1994 | Baker et al. | 424/435 |
| 5,968,547 | 10/1999 | Reder et al. | 424/449 |
| 6,143,320 | * 11/2000 | Becher et al. | . |

FOREIGN PATENT DOCUMENTS

| | | | |
|---|---|---|---|
| 9642043 | 10/1996 | (DE) | A61L/15/44 |
| 0432945 | 11/1990 | (EP) | A61L/15/44 |
| 0581057 | 7/1993 | (EP) | A61K/9/70 |
| 9119474 | 12/1991 | (WO) | A61F/13/00 |
| 9219226 | 11/1992 | (WO) | A61K/9/16 |
| 9836728 | 8/1998 | (WO) | . |

* cited by examiner

*Primary Examiner*—Thurman K. Page
*Assistant Examiner*—Isis Ghali
(74) *Attorney, Agent, or Firm*—James E. Klaniecki; Ann W. Speckman

(57) ABSTRACT

Methods for the treatment of patients are provided, such methods comprising applying to the patient a transdermal therapeutic system comprising a therapeutically effective substance such that the dosage of the therapeutically active substance remains constant over a prolonged period of time.

7 Claims, No Drawings

METHOD FOR TRANSDERMAL APPLICATION OF ACTIVE SUBSTANCES AT HIGH CONSTANT DOSAGE

This is a continuation-in-part of co-pending U.S. patent application Ser. No. 09/173,804 filed Oct. 16, 1998 now U.S. Pat No. 6,143,320 and of International Patent Application PCT/EP98/06607 filed Oct. 19, 1998, which designated the U.S., and of German Patent No. DE 197 46 191.3, filed October 18, 1997.

The invention relates to a method of treating patients with transdermal therapeutic systems containing active substance, said method ensuring the constant dosage over a prolonged period, especially for the treatment of patients with narcotics or drug dependency or patients suffering with painful conditions.

WO 93/19226 relates to a drug delivery system useful in treating an individual for a drug dependency. The drug delivery system, which may be a transdermal patch, is capable of delivering active substances, preferred lobeline, to an individual in a controlled, sustained release manner and providing long-term therapeutic levels of active substances to the individual. The transdermal patch is applied for the time of at least one day, preferably seven days and is removed before applying a new one.

EP-A1-0 432 945 discloses a transdermal delivery system for the treatment of cocaine and heroin addiction in a human or animal subject, which includes as the active ingredient buprenorphine. The transdermal delivery system is capable to deliver and maintain blood levels of from about 0.1 milligram to about 0.6 milligram.

WO 91/19474 relates to a method of making an laminated composite for administering buprenorphine transdermally to treat pain.

DE-A1-196 42 043 is directed to a transdermal therapeutic system for the delivery of active substances for the treatment of drug addicts. A preferred agent for this treatment is burpenorphin.

U.S. Pat. No. 5,362,496 discloses a method for treating conditions responsive to nicotine therapy, which utilizes transdermal nicotine delivery for obtaining base-line nicotine plasma levels. A transdermal patch containing a high load of nicotine is first administered for a period of several weeks and is then replaced by a transdermal patch containing a lower loading of nicotine.

U.S. Pat. No. 5,968,547 pertains to a method of treating pain or opioid addiction in patients by utilizing a transdermal delivery system containing buprenorphin. The method comprises transdermal delivery of buprenorphine at first at a high release rate and subsequently at a lower release rate either with the same delivery system or upon removal of the system and replacement with a different transdermal system.

U.S. Pat. No. 5,026,556 discloses a composition for transdermal delivery of buprenorphine.

Transdermal forms of administration provide important advantages for the treatment of dependencies such as narcotics or drug addiction, and for analgesia; compared to oral or parenteral forms:

1. The improper extraction of active substances and, consequently, "dealing" of the pure active substance is extremely difficult and expensive and thus normally impossible and pointless for addicts.
2. The absorption of the medicinal agent can easily be monitored by surveillance of the blood level.
3. Administration can be interrupted at any time if an addict additionally takes, for example, the drug of addiction during the treatment, in contravention of the rules.
4. Transdermal administration is suitable for achieving a constant blood level of the active substance.

In many cases, however, the relatively high blood plasma concentrations required for the treatment of certain illnesses cannot be reliably achieved using those administration forms of transdermal systems (TTS) that are available on the market. This also applies, in particular, to the transdermal administration of buprenorphine. In addition, dosing by means of a patch of increased surface area is not accepted owing to the reduced level of wear comfort that it entails. In addition, the required dosing with a patch would not be able to achieve a constant blood level by an increase in its surface area because the pharmacokinetics of such a patch cannot readily be adjusted such that it is possible to obtain a constant, higher blood level over the desired time period of, for example, seven days or more.

Consequently, it is the object of the invention to provide a method for transdermal administration of active substances by means of transdermal therapeutic systems for treating illnesses, especially painful conditions, and for suppressing or alleviating an addiction such as narcotics or drug addition, by means of which method it is possible to achieve a blood plasma level of active substances which is approximately constant and sufficiently high for successful therapy over a reasonable and useful period of treatment—for example, seven days or more.

In order to achieve the above said object the invention proposes the application, as part of a predetermined therapeutic plan, of two or more active substance patches sequentially with a temporal overlap and accompanied by monitoring of the blood level of the active substance, so as to achieve a blood level of active substance which is sufficiently high for successfully suppressing the addiction and remains constantly effective over a useful period of use. The overlapping application of two or more active substance TTS, either sequentially or in alternation, should meet with sufficient acceptance in the case of the target indications. The application of the method of the invention for the treatment of drug addicts is made even easier by the fact that such persons are in any case to be examined, usefully at relatively short intervals, i. e., at least every three or four days, to ascertain any additional consumption of a drug of addiction, which could be harmful to the therapy, or other health disturbances.

The active substances which can be used in accordance with the invention are those which are suitable in principle for administration by means of transdermal therapeutic systems, examples being nicotine, corticosteroids such as hydrocortisone, prednisolone, antiinflammatories such as acetaminophen, diclofenac and phenylbutazone; sedatives such as phenobarbital, triazolam, and haloperidol; tranquillizers such as fluphenazin and lorazepam; antihypertensives such as nifedipine; antiepileptics such as meprobamate; coronary vasodilators auch as dipyridamol; antihistamines such as diphenylhydramine hydrochloride and diphenylimidazole; sex hormons such as estradiol, testostereone, and progesterone; analgesics such as ibuprofen, acetylsalicylic acid, naproxen, buprenorphine, and other pharmaceuticals. The active substances used to control or treat addiction or dependencies are generally substitutes, examples being methadone, naltrexone or buprenorphine for the treatment of heroin dependency, buprenorphine, desipramine or amfabutamone for the treatment of cocaine dependency, naltrexone, busperone or disulfiram for the treatment of alcohol dependency, and benzodiazepines having a relatively long half-life, such a diazepam or flurazepam, for example, for treating dependency on benzodiazepines. A certain number of the abovementioned active substances, especially buprenorphine, can also be used as analgesics for treating painful conditions.

One embodiment provides that a useful period of administration with a predetermined blood level of active substance is achieved through the use of two or more plasters in sequence and with a temporal overlap over at least seven days.

By this means, in the case, for example, of drug addicts, a gradual decrease in the addictive potential over a prolonged period can be achieved in conjunction with optimum wear comfort, and thus effect of the addiction can be gradually reduced.

One preferred embodiment provides for a treatment cycle according to which first of all a transdermal therapeutic system having a defined application period of several days is applied and before the expiry of half the period of time within which the active substance content of the TTS is almost exhausted—for example, after 3 days—and especially before the onset of a flatting-out of the blood plasma concentration of the active substance, a further TTS—overlapping temporally the duration of action of the first—is applied.

One particularly advantageous and preferred embodiment of the method of using a patch comprising the active substance buprenorphine provides that at least two TTS are used first of all; subsequently, before reaching the expiry of half the period of time within which the active substance content of the TTS is virtually exhausted, a further, preferred TTS is applied sequentially; after a few days of action, especially when the active substance content of the first TTS is exhausted, but in any case before a perceptible flatting-out of the predetermined blood level, a further TTS is applied sequentially and so on, and that the first TTS is removed from the skin, likewise sequentially, on reaching their point of exhaustion, and a plurality of treatment cycles are applied in this way.

One application of the process according to the invention is envisaged for a therapeutic effect over several days by means of TTS with which the dosage rate and dosage duration required for successful addiction control cannot be achieved by means of a single TTS.

A utilization according to the invention is described by way of example by the following treatment:

A TTS having a defined application period of seven days is used together with a second such TTS. Alfter three days—i. e., before the onset of a flattening-out of the blood levels—a third "fresh" TTS is used, so that a constant blood level is ensured. After seven days from the application of the first TTS it is possible, in turn, to apply a fourth TTS, after a further three or four days a fifth, an so on.

The following scheme illustrates the exemplified treatment:

| | | |
|---|---|---|
| 0 days | Application of 2 TTS (A) | |
| 3 days | Application of 1 TTS (B) | Cycle 1 (day 0 to day 7) |
| 7 days | Removal of 1 TTS (A) and application of 1 TTS (C) | |
| 10 days | Removal of 1 TTS (B) and application of 1 TTS (D) | Cycle 2 (day 7 to day 14) |
| 14 days | Removal of 1 TTS (C) and application of 1 TTS (E). | |

The invention is judicious, it meets an urgent need for transdermal treatment of patients suffering from an illness, or narcotics or drug addicts, with therapeutic means which already exist per se, and it presents in particular a safe way of reducing dangers of addiction without the need for prolonged and costly new research. The invention is thus an ideal means of achieving the object stated at the outset.

What is claimed is:

1. A method of transdermal treatment of a patient suffering from an illness or painful conditions or a patient with drug or narcotics dependency by administering to said patient transdermal therapeutic systems comprising a therapeutically effective active substance in order to ensure a blood plasma concentration of the active substance which is approximately constant over a useful application period, which comprises applying to the patient said transdermal therapeutic system in at least one treatment cycle, each cycle comprising several days and comprising the following steps:

(a) application of at least one transdermal therapeutic system, comprising the active substance, with a defined application period of several days;

(b) application of at least one further transdermal therapeutic system, comprising the active substance, before the expiry of half the period of time within which the active substance content of the initially applied transdermal therapeutic system(s) is substantially exhausted;

(c) removal of the initially applied transdermal therapeutic system(s) when its (their) active substance contents is (are) substantially exhausted.

2. The method as claimed in claim 1, wherein the second treatment cycle begins with the application of at least one transdermal therapeutic system, comprising the active substance, simultaneously with the removal of the transdermal therapeutic system(s), applied in the first cycle, from the skin of the patient.

3. The method as claimed in 1 or 2, wherein the patient has an opiate dependency.

4. The method as claimed in claim 3, wherein the patient has a heroin or cocaine dependency.

5. The method as claimed in claim 1 or 2, wherein the patient is suffering from painful conditions.

6. The method as claimed in claim 1 or 2, wherein the active substance is buprenorphine.

7. The method as claimed in claim 1, wherein a treatment cycle comprises 7 days, at least two transdermal therapeutic systems comprising the active substance being applied at the beginning of the cycle, a further transdermal therapeutic system comprising the active substance being applied after 3 days, and after 7 days the transdermal therapeutic systems applied initially being removed from the skin of the patient.

* * * * *

UNITED STATES PATENT AND TRADEMARK OFFICE
CERTIFICATE OF CORRECTION

PATENT NO. : 6,280,766 B1 Page 1 of 1
DATED : August 28, 2001
INVENTOR(S) : Frank Becher and Werner Wessling It is certified that error appears in the above-identified patent and that said Letters Patent is hereby corrected as shown below:

<u>Title page,</u>
Replace "[63] Continuation-in-part of application No. 09/173,804, filed as application No. PCT/EP98/06607 on Oct. 18, 1998, now Pat. No. 6,143,320" with -- continuation-in-part of co-pending U.S. Patent Application Ser. No. 173,804 filed Oct. 16, 1998 and of International Patent Application PCT/EP98/06607 filed Oct. 19, 1998, which designated the U.S. --

Signed and Sealed this

Twentieth Day of August, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,280,766 B1
DATED : August 28, 2001
INVENTOR(S) : Frank Becher and Werner Wessling It is certified that error appears in the above-identified patent and that said Letters Patent is hereby corrected as shown below:

<u>Title page,</u>
Replace Item "[73], Assignee: LTS Lehman Therapie-Systeme GmbH, Neuwied (DE)" with Item -- [73], Assignee: LTS Lohmann Therapie-Systeme AG, Neuwied (DE) --

Signed and Sealed this

Eighteenth Day of March, 2003

JAMES E. ROGAN
*Director of the United States Patent and Trademark Office*